(12) United States Patent
Adams et al.

(10) Patent No.: US 6,497,686 B1
(45) Date of Patent: Dec. 24, 2002

(54) METHOD AND APPARATUS FOR PERFORMING STERILE MEDICAL PROCEDURES

(75) Inventors: Ronald D. Adams, Holliston, MA (US); Roy H. Sullivan, Millville, MA (US)

(73) Assignee: SCIMED Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/556,690

(22) Filed: Apr. 21, 2000

(51) Int. Cl.[7] ............................................. A61M 25/00
(52) U.S. Cl. .................. 604/268; 604/164.01; 604/212; 604/258
(58) Field of Search ............................. 604/158, 93.01, 604/117, 164.01, 164.02, 164.04, 164.06, 164.07, 167.01, 167.06, 181, 187, 212, 214, 216, 258, 268

(56) References Cited

U.S. PATENT DOCUMENTS

| | | | |
|---|---|---|---|
| 4,387,879 A | | 6/1983 | Tauschinski |
| 4,645,495 A | | 2/1987 | Vaillancourt |
| 4,767,411 A | | 8/1988 | Edmunds |
| 4,828,547 A | * | 5/1989 | Sahi et al. ............. 604/164.06 |
| 4,846,799 A | * | 7/1989 | Tanaka et al. ............... 604/158 |
| 5,207,652 A | | 5/1993 | Kay |
| 5,306,239 A | * | 4/1994 | Gurmarnik et al. ..... 604/164.01 |
| 5,308,322 A | | 5/1994 | Tennican et al. |
| 5,338,308 A | | 8/1994 | Wilk |
| 5,355,871 A | * | 10/1994 | Hurley et al. ................ 604/212 |
| 5,531,692 A | * | 7/1996 | Rogers ........................ 604/181 |
| 5,713,874 A | * | 2/1998 | Ferber .......................... 604/158 |
| 5,715,815 A | | 2/1998 | Lorenzen et al. |
| 5,743,891 A | * | 4/1998 | Tolkoff et al. .......... 604/164.01 |
| 5,817,073 A | | 10/1998 | Krespi |
| 5,882,331 A | * | 3/1999 | Sasaki .................... 604/164.01 |
| 6,083,202 A | * | 7/2000 | Smith ..................... 604/164.01 |
| 6,277,100 B1 | * | 8/2001 | Raulerson et al. ........... 604/212 |

FOREIGN PATENT DOCUMENTS

| | | |
|---|---|---|
| EP | 0 872 215 | 10/1998 |
| WO | 96/23536 | 8/1996 |
| WO | 99/13928 | 3/1999 |

* cited by examiner

*Primary Examiner*—Teresa Walberg
*Assistant Examiner*—Fadi H. Dahbour
(74) *Attorney, Agent, or Firm*—Finnegan, Henderson, Farabow, Garrett & Dunner,LLP

(57) ABSTRACT

A method and related device for performing sterile medical procedures are disclosed. The method and related device are capable of accessing a sterile environment from a non-sterile environment to perform a medical procedure within the sterile environment. The method and related device can achieve a sterile technique during endoluminal procedures and in uncontrolled and unsterile environments. The device includes an inner hollow member moveably disposed within an outer hollow member. The outer hollow member is adapted to penetrate a boundary separating non-sterile and sterile environments and the inner hollow member is adapted to extend past the outer hollow member and into the sterile environment. A fluid compartment is adapted to be in selective fluid communication with the outer tube such that when the inner member extends past the outer member and into the sterile environment, fluid enters the outer member and the boundary.

53 Claims, 3 Drawing Sheets

METHOD AND APPARATUS FOR PERFORMING STERILE MEDICAL PROCEDURES

FIELD OF THE INVENTION

The present invention pertains to a method and related device used to provide access from a non-sterile environment to a sterile environment. More specifically, the invention relates to a sterile technique used during a medical procedure, such as disease treatment and/or diagnosis, taking place in lumens within a body. Such endoluminal procedures may take place in vascular, gastrointestinal, air exchange lumens, or other like places within the body and often require passing a device through the lumen wall to access a sterile environment.

BACKGROUND OF THE INVENTION

Generally, medical practitioners have practiced and refined sterile techniques to prevent microbial contamination when passing objects such as catheters, other surgical tools, hands, fingers, medications, and the like from a non-sterile environment to a sterile environment. Implementing a sterile technique requires that the objects themselves remain microbe-free when entering the sterile environment. Additionally, the opening between the non-sterile and sterile environments must remain impassable to microbes for a time period sufficient to allow completion of the medical procedure and closure of the breach between the environments.

For a number of medical procedures, these requirements are more readily met. Such medical procedures occur in areas of the body that easily can be kept clean, dry and free from contamination for extended time periods. Moreover, many medical procedures occur in environmentally controlled surgical arenas, thus facilitating a sterile technique.

Many currently-employed methods and devices focus on avoiding contamination at catheter insertion sites on the patient's body. Some of these methods and devices may attempt to stabilize the catheter and to apply antiseptic solutions at the insertion site. Such devices may include an adhesive patch or seal that surrounds the catheter and affixes to the patient's skin. Additionally, the devices may include a mechanism for feeding antiseptic solution between the skin and the patch or seal. Overall, these systems attempt to apply a sterile technique at the boundary between the atmosphere (the non-sterile environment) and a point of insertion on the patient's body. However, the current systems are not suited for performing a sterile technique at intracorporeal sites, for example the boundary between a gastrointestinal lumen (non-sterile environment) and the inter-abdominal cavity (sterile environment).

Achieving a sterile technique for many intracorporeal sites can pose difficulties. For instance, keeping an area of the body clean, dry, and free from contamination presents significant challenges when the treatment area exists in a part of the body awash with microbe-rich body fluids. An endoluminal procedure presents such a challenge. During an endoluminal procedure, diagnostic or treatment devices pass through a lumen wall to access other areas within the body, for example, entering the inter-abdominal cavity from the gastrointestinal tract, as mentioned earlier. Because body lumens generally are microbe-rich environments, a significant risk of infection arises due to the potential for the lumen fluids to leak through the hole formed in the lumen wall and into the sterile environment. Such infection can cause serious illness, such as sepsis, and even death.

Successful implementation of a sterile technique also may prove difficult when treatment proceeds under less than ideal environmental conditions. For example, medical procedures and treatments often take place on a battlefield or during a rescue operation where controlling and sterilizing the surrounding environment may be nearly impossible.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

To attain the advantages and in accordance with the purpose of the invention, as embodied and broadly described herein, the invention includes a device for performing a sterile technique. According to a preferred embodiment of the invention, the device includes an outer hollow member having a sharp distal end for penetrating a tissue that separates a sterile environment from a non-sterile environment. The outer hollow member also has a seal at its sharp distal end. The device further includes an inner hollow member disposed within the outer hollow member and axially moveable with respect to the outer hollow member. The inner hollow member also has a sharp distal end for penetrating the tissue and extending into the sterile environment.

In another preferred embodiment of the invention, the device includes a distal end capable of penetrating a boundary layer separating a non-sterile environment from a sterile environment and an inner hollow member moveably disposed within the outer hollow member. The inner hollow member includes a distal end adapted to extend past the outer hollow member distal end and into a sterile environment. The device further includes a compartment containing a reservoir of antiseptic solution, with the reservoir in selective fluid communication with the outer hollow member so that when the inner hollow member extends into the sterile environment, the antiseptic solution flows through the outer hollow member to create a sterile boundary.

The invention further includes a method of performing a sterile medical procedure by creating a sterile passage. A preferred method includes penetrating a tissue separating a sterile environment from a non-sterile environment with a sharpened distal end of an outer hollow member, with the distal end of the outer hollow member including a seal. The method further includes extending a sharpened distal end of an inner hollow member in an axial direction with respect to the outer hollow member and penetrating the seal and the tissue so that the distal end of the inner hollow member enters the sterile environment.

Another preferred method according to the present invention includes penetrating a non-sterile/sterile boundary with a distal end of an outer hollow member, and providing an inner hollow member that is moveably disposed within the outer hollow member. The method further includes extending a distal end of the inner hollow member past the outer hollow member distal end and into the sterile environment, and providing a compartment containing a reservoir of antiseptic solution and selectively establishing fluid communication between the reservoir and the outer hollow member such that during the extending step, the antiseptic solution flows through the outer hollow member to enable a sterile technique.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate the preferred embodiment of the invention and, together with the description, serve to explain the principles of the invention. In the drawings.

DESCRIPTION OF THE PREFERRED EMBODIMENT

This invention generally pertains to a method and related device for performing a sterile technique during medical procedures. The device and method prevent contamination of a sterile environment when accessed from a non-sterile environment during a procedure that, for example, passes an object from the non-sterile environment to the sterile environment. The method, and its related device, has the capability of achieving sterile techniques intracorporeally, for example during an endoluminal procedure. The method and device, however, are not limited to intracorporeal sites of a body and can be used to gain access to any sterile environment within the body from any adjacent non-sterile environment. Furthermore, the method and related device can perform a sterile technique in an unclean and uncontrolled environment, such as a battlefield or rescue site.

Use of the device according to the present invention, however, is not necessarily limited to medical applications. The inventive device may be used to gain access to a sterile environment from a non-sterile environment when needed in non-medical applications in industry or otherwise. Moreover, the medical applications are not limited to the human body and instead extend to bodies of other animals.

To accomplish the objectives stated above and to overcome the problems associated with existing devices of this kind, preferred embodiments of the present invention provide features such as a self-contained unit for carrying, for example, an antiseptic solution and applying the solution to an operative site, a mechanism for intracorporeal sterile technique, and a post-sealing system to prevent contamination from the external environment after completing the medical procedure. The device of the present invention, preferably incorporates inner and outer insertion tubes. The outer insertion tube partially penetrates the non-sterile/sterile boundary and the inner insertion tube completes entry into the sterile environment. As mentioned, the device may include a self-contained reservoir of, for example, antiseptic solution for further preventing contamination of the sterile environment. The self-contained reservoir also facilitates portage of the necessary medical equipment since a user will not be required to carry antiseptic solution in a separate container. The sealing system closes off the insertion point from the surrounding environment to keep the sterile environment contaminant-free after completion of the medical procedure.

Reference will now be made in detail to the present exemplary embodiments of the invention, examples of which are illustrated in the accompanying drawings. Wherever possible, the same reference numbers will be used throughout the drawings to refer to the same or like parts.

Figure 1:
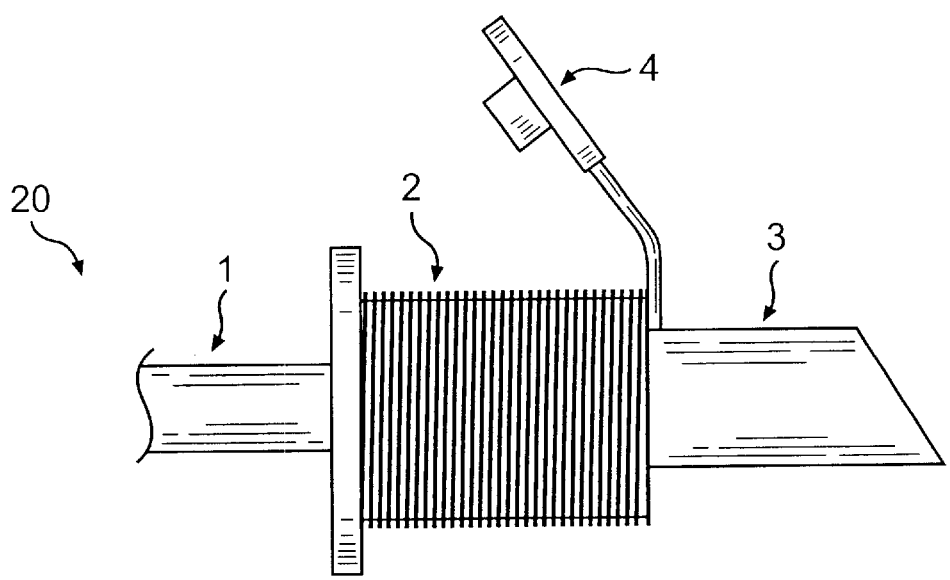
FIG. 1 is a plan view of an embodiment of the device of the present invention.

In accordance with a preferred embodiment of the present invention, a device 20 for performing a sterile technique is shown generally in FIG. 1. The device 20 includes a catheter 1 through which medical devices, medication, and the like can be inserted to perform a medical procedure, including an endoluminal procedure. Device 20 further includes a collapsible compartment 2 for containing, for example, antiseptic solution, an outer insertion tube 3, and a cap 4 for post-procedure sealing.

Figure 2:
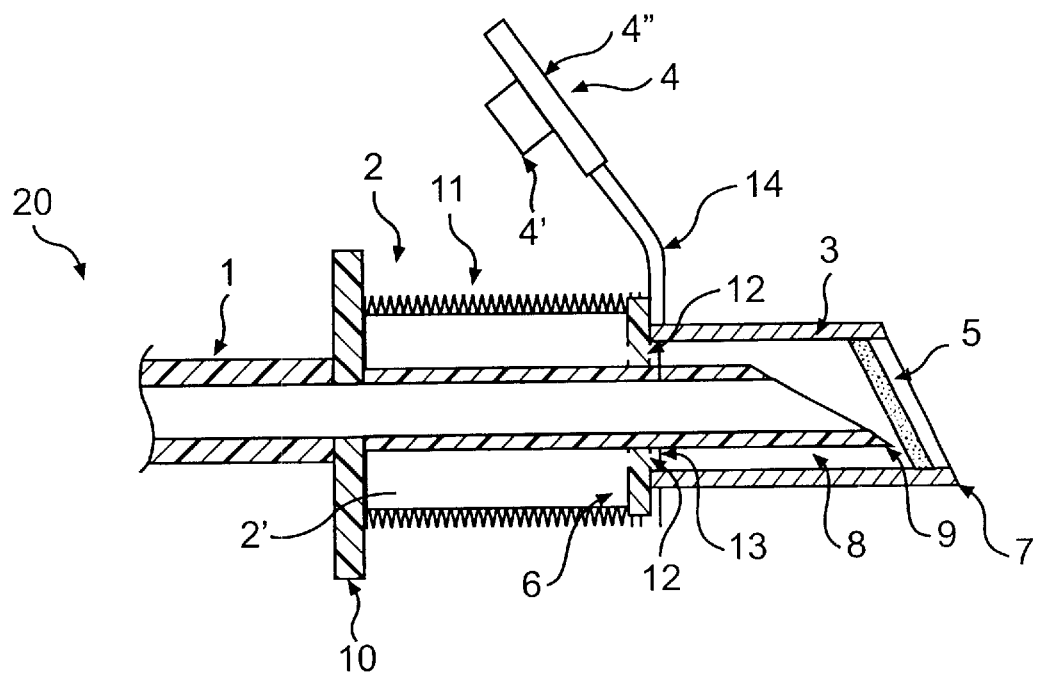
FIG. 2 is a cross-sectional view of the device of FIG. 1.

More detail of these and other structural features of device 20, and their relation to one another, is illustrated in the cross-sectional view of FIG. 2. Thus, as shown, outer tube 3 includes a sharpened distal end 7 capable of penetrating layers of skin, muscle, and other kinds of tissue. Outer insertion tube 3 also includes a seal 5 at distal end 7. Distal end seal 5 keeps the interior of outer tube 3 and its contents, including inner tube 8, sterile before and during use of the device. Seal 5 may be any suitable seal known in the art that prevents contaminants from entering tube 3, yet permits penetration by an inner tube 8, to be described later. Such seals may include, for example, trocar and PEG tube seals.

A proximal end of outer insertion tube 3 attaches to collapsible compartment 2 at a partition 6. Partition 6, which will be described in more detail herein, prevents premature leakage of, for example, antiseptic solution from a compartment reservoir 2' into outer tube 3.

Slidably disposed within outer tube 3 is an inner insertion tube 8. Inner tube 8 moves axially relative to and within outer tube 3. Like outer tube 3, inner tube 8 has a sharpened distal end 9 capable of penetrating layers of skin and tissue, as well as outer tube seal 5. At its proximal end, inner tube 8 fixedly attaches to a proximal end plate 10 that seals collapsible compartment 2 from the surrounding environment. Inner tube 8 extends from end plate 10, through compartment reservoir 2' and partition 6, and into outer tube 3. In addition to slidably moving within outer tube 3, inner tube 8 slidably moves relative to partition 6. Flexible catheter 1 attaches to end plate 10 on the side of end plate 10 opposite reservoir 2'. Moreover, the lumen of catheter 1 fluidly connects with the lumen of inner insertion tube 8 so that sterile fluids, medication, or other catheter-based endoluminal devices can pass through catheter 1, into inner tube 8, and ultimately into the sterile environment.

A preferred aspect of the device of the present invention is collapsible compartment 2. Collapsible compartment 2 can be made of ribbed silicone rubber, bellows made of a synthetic rubber material, or some other suitable like material and structure that allows the compartment to collapse while also substantially preventing fluid leakage from the compartment. Collapsible compartment 2 defines a reservoir 2' that preferably contains an antiseptic solution or other sterilization fluid during use. The reservoir 2' is further defined by the distal end of end plate 10, the proximal end of partition 6, and the outer surface of inner tube 8. Prior to insertion of inner tube 8 into a sterile environment, compartment 2 prevents leakage of antiseptic solution out of reservoir 2' through the sealed connection between end plate 10, outer collapsible wall 11, partition 6, as well as between end plate 10 and catheter 1, and partition 6 and inner tube 8. The engaged relationship between compartment 2 and partition 6 further includes a light plastic weld. The weld can be broken upon twisting of compartment 2 with respect to partition 6 at the end of a medical procedure to separate compartment 2 from partition 6.

Partition 6 has perforations 12 forming channels through which antiseptic solution can flow from reservoir 2' to outer tube 3. The cross-sectional view of FIG. 2 shows two such perforations. It is contemplated that any number or size perforations spaced around partition 6 may be used. A thin membrane 13 attaches to or otherwise lies over perforations 12 to prevent premature leakage of the solution into outer tube 3. Membrane 13 can be on either side of partition 6 to cover perforations 12, and essentially operates as a one-way valve.

Upon actuation of device 20, i.e., upon compression of collapsible compartment 2, membrane 13 bursts either due to the pressure of the solution within compartment 2 or alternatively due to the linear motion of inner tube 8. In either case, bursting membrane 13 uncovers perforations 12, allowing antiseptic solution to flow into outer tube 3. Membranous seal 13 can be made of plastic or other suitable material that can act as a fluid seal, yet rupture under pressures achieved by the solution in reservoir 2' as a result of collapsing compartment 2. Overall, the structural features of collapsible compartment 2, partition 6, and membranous seal 13 facilitate portability of necessary medical equipment so that sterile conditions can be achieved even in unsterile and uncontrolled surrounding environments without the need to carry separate containers of antiseptic solution.

Cap 4 attaches to a peripheral surface of outer tube 3 by a flexible tether 14. Cap 4 has a small diameter portion 4' sized to fit sealingly within the opening in partition 6 through which inner tube 8 extends. A larger diameter portion 4" is sized to cover perforations 12 when cap 4 is secured into place in partition 6. In post-procedure use, cap 4 bars entry into a sterile environment of septic materials or other contaminations existing in surrounding, non-sterile environment. Cap 4 and tether 14 can be made of biodegradable plastic or some other suitable like material.

Figure 3:
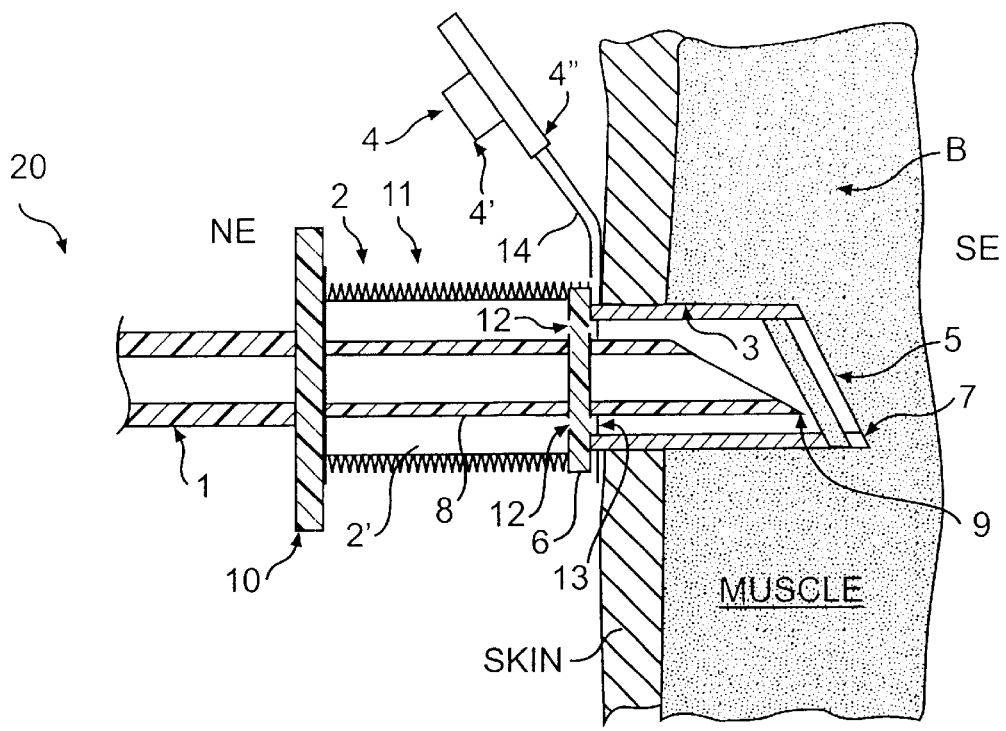
FIG. 3 is a cross-sectional view of the device of FIG. 1 during insertion into a boundary layer separating non-sterile and sterile environments.

Operation of device 20 in performing a sterile technique will now be explained with reference to FIGS. 3 to 5. As shown in these Figures, device 20 accesses a sterile environment SE from a non-sterile environment NE through a boundary B of, for example, skin and muscle. Boundary B also can be made of other body tissues such as mucosa, fat tissue, fibrous tissue or other similar body tissues and combinations thereof. The boundary of skin and muscle shown in the Figures is for illustrative purposes only and is not meant to limit the invention. It is further contemplated that the device access the sterile environment through a boundary consisting of a lumen wall, as in the case of endoluminal procedures discussed previously.

Initially, pressure is placed on device 20, preferably at end plate 10, so that sharpened distal end 7 of outer tube 3 punctures an outer layer (in this case, a skin layer) of boundary B exposed to non-sterile environment NE. As the application of pressure continues, sharpened distal end 7 drives through a thickness of boundary B, including other tissue layers such as the muscle layer shown in the Figures. Outer tube 3 penetrates through boundary B until partition 6 abuts the outer layer of boundary B exposed to non-sterile environment NE, the position shown in FIG. 3. The length of outer tube 3 should be selected such that distal tip 7 does not enter sterile environment SE when partition 6 abuts the outer boundary layer and instead remains entirely within boundary B. It is contemplated that differing lengths of outer tube may be used for different types and thicknesses of tissue.

Figure 4:
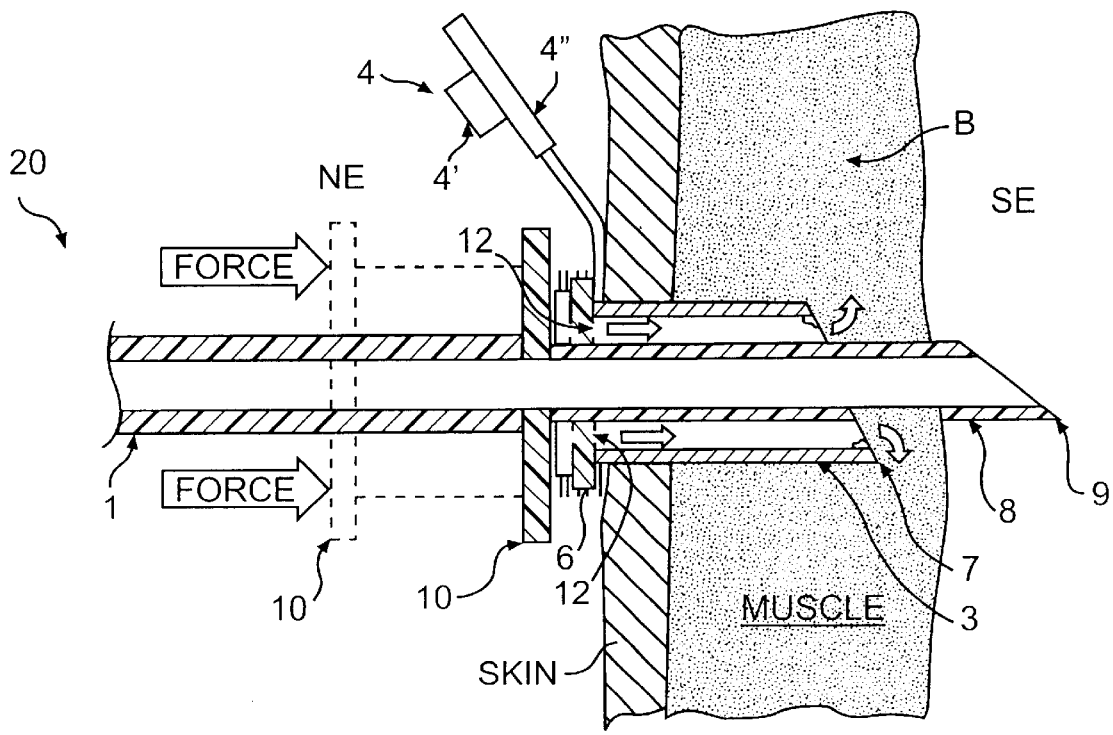
FIG. 4 is a cross-sectional view of the device of FIG. 1 during entry into a sterile environment.
Figure 5:
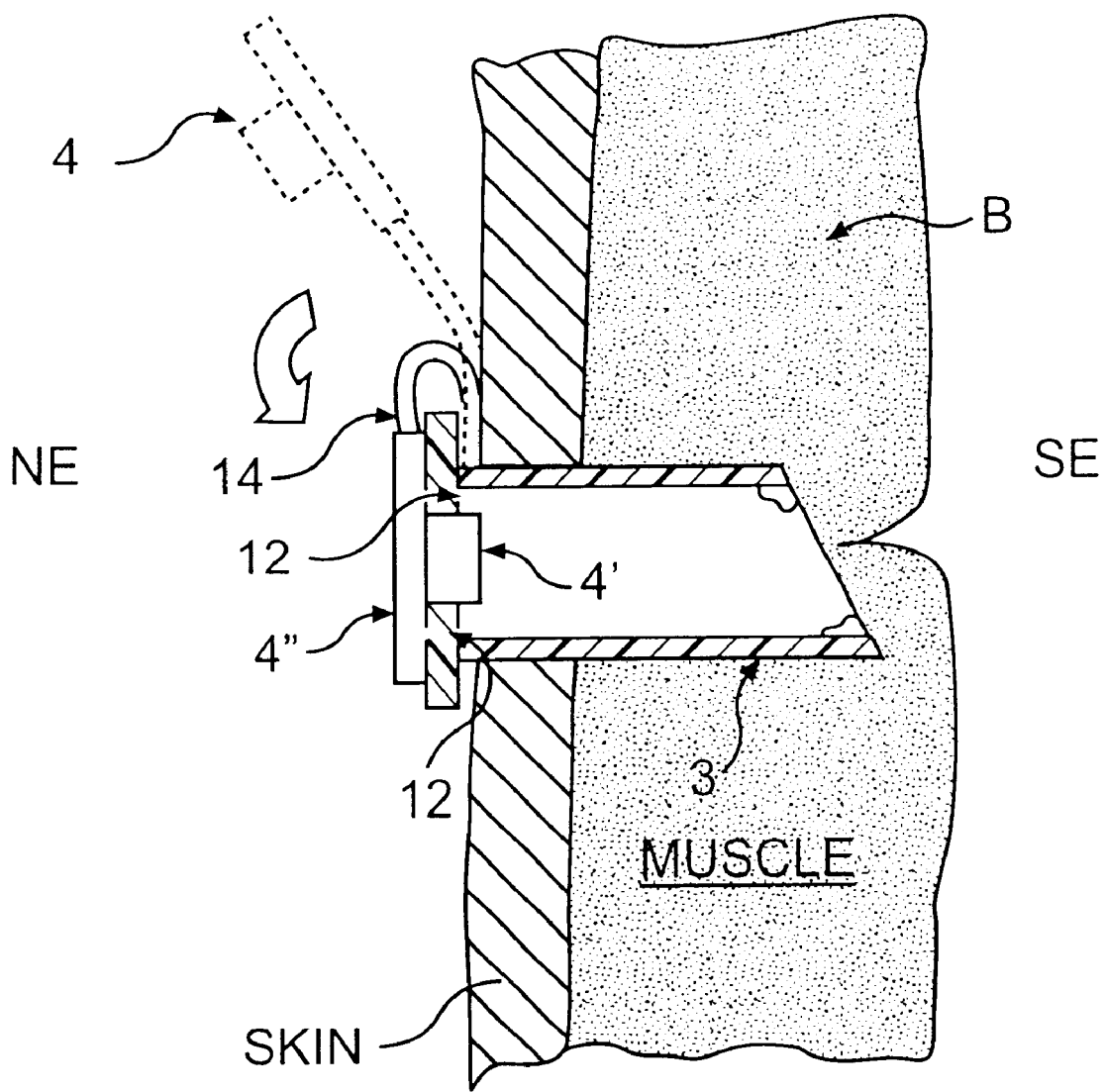
FIG. 5 is a cross-sectional view of an outer insertion tube and cap of the device of FIG. 1 during sealing of the sterile environment after a medical procedure has been completed.

After outer tube 3 has been inserted into boundary B so that partition 6 abuts boundary B, the user compresses collapsible compartment 2 by applying force on end plate 10, as shown in FIG. 4. As compression of compartment 2 proceeds, the pressure in reservoir 2' increases. This increase in pressure causes membranous seal 13 to burst, allowing antiseptic solution from reservoir 2' to flow through perforations 12. Thus, antiseptic solution fills outer tube 3 and surrounds and sterilizes inner tube 8.

As end plate 10 moves toward partition 6, inner tube 8 moves through outer tube 3. Sharpened distal tip 9 of inner tube 8 eventually pierces outer tube seal 5, releasing the antiseptic solution previously trapped in outer tube 3. The antiseptic solution flows into the surrounding tissue of boundary B, killing any microbes that may have been introduced into boundary B during the initial insertion of device 20. Inner tube distal tip 9 continues to advance through seal 5 of outer tube 3, through boundary B, and into sterile environment SE until compartment 2 completely collapses, as shown by the solid lines in FIG. 4. Due to the release of antiseptic solution from outer tube 3 into boundary B and the sterilization of inner tube 8, inner tube 8 enters sterile environment SE microbe-free. Thus, a sterile technique is accomplished and sterile fluids, catheter-based medical devices, medications, and the like can be fed through catheter 1 into sterile environment SE without risk of contamination.

After performing the desired medical procedure within sterile environment SE, any catheter-based or endoluminal devices that were used are removed from catheter 1. End plate 10 and compartment 2 are then twisted to break the welded seam between compartment 2 and partition 6. The seam between compartment 2 and partition 6 must be strong enough to resist premature rupture and yet be fragile enough to break off for post-procedure purposes. It is contemplated that plastic will be used for the welded seam, however, other suitable like materials and methods of connection exhibiting the desired strength characteristics also can be used.

Once compartment 2 and partition 6 are separated, catheter 1, collapsible compartment 2, and end plate 10 with attached inner tube 8 are pulled away from the rest of device 20 and can be disposed of safely as required. Outer tube 3 remains within boundary B and partition 6 remains abutting against boundary B on the side exposed to non-sterile environment NE, as shown in FIG. 5. By inserting small diameter portion 4' of cap 4 into partition 6, with larger diameter portion 4" covering perforations 12, cap 4 effectively seals the interior of outer tube 3 from surrounding non-sterile environment NE. Therefore, both sterile environment SE and the wound caused by insertion of the device are kept contamination-free after the medical procedure. The solid lines of FIG. 5 illustrate the placement of post-procedural sealing cap 4 with respect to partition 6 and outer tube 3.

The device 20 preferably is a single use device. However, the portions of device 20 that are removed after the medical procedure (catheter 1, compartment 2, end plate 10, and tube 8) may be sterilized and appropriately affixed to a new outer tube 10, cap 4, and partition 6 for re-use.

The portions of the device that remain after the medical procedure is performed are preferably made of biodegradable plastic suture material or other suitable implantable materials such as stainless steel and titanium. Other possible materials that are biodegradable and biocompatible are also contemplated by this invention. After a time sufficient to allow the wound to form a scab and heal, the material biodegrades and the device disappears. Suitable biodegradable materials are known to those having ordinary skill in the art.

A further aspect of the device includes the use of pressure gradients to ensure movement of materials only from sterile to non-sterile environments and not vice versa when openings are formed. For instance, an insufflation pump could be used to maintain a positive pressure into the working cavity. That is, the pump would be configured to create a higher pressure outside of the working cavity as compared to the pressure inside the cavity.

It will be apparent to those skilled in the art from consideration of the specification and practice of the invention disclosed herein that various modifications and variations can be made in the sterile technique method and related device according to the present invention. For example, biodegradable plastic has been suggested as the material to be used in forming the device, but one having ordinary skill in the art would recognize that other materials having similar properties could be utilized as well. Also, the sizes and shapes of the various components, including the inner and outer tubes and the compartment, of the device may differ from one embodiment to the next depending on the medical procedure to be performed. Various changes in size and shape may also be necessary depending on the types and thicknesses of the boundaries between the non-sterile and sterile environments.

Therefore, the invention in its broader aspects is not limited to the specific details and illustrative examples shown and described in the specification. It is intended that departures may be made from such details without departing from the true spirit or scope of the general inventive concept as defined by the following claims and their equivalents.

What is claimed is:

1. A device for performing sterile medical procedures, comprising:
   an outer hollow member including a distal end capable of penetrating a boundary layer separating a non-sterile environment from a sterile environment;
   an inner hollow member moveably disposed within the outer hollow member, said inner hollow member including a distal end adapted to extend past said outer hollow member distal end and into a sterile environment; and
   a compartment defining a reservoir in selective fluid communication with said outer hollow member so as to flow fluid into a portion of said outer hollow member surrounding said inner hollow member.

2. The device of claim 1, wherein said reservoir is for containing a solution to sterilize said inner hollow member and said boundary layer adjacent said outer hollow member.

3. The device of claim 1, wherein the hollow members are tubes.

4. The device of claim 1, wherein said compartment includes a partition separating said reservoir and said outer hollow member.

5. The device of claim 4, wherein said partition includes perforations for selective fluid communication between said reservoir and said outer hollow member.

6. The device of claim 5, further comprising a breakable sealing member for sealing said perforations prior to said selective fluid communication.

7. The device of claim 6, wherein said sealing member includes a plastic membrane.

8. The device of claim 4, further comprising a sealing member adapted to engage with said partition to seal said outer hollow member so that said sterile environment is sealed from said surrounding non-sterile environment.

9. The device of claim 8, wherein said sealing member includes a cap having a first portion adapted to fit within an opening in said partition.

10. The device of claim 9, wherein the partition includes perforations for selective fluid communication between said reservoir and said hollow outer member, and said cap includes a second portion adapted to seal said perforations.

11. The device of claim 1, wherein said compartment is adapted to collapse.

12. The device of claim 1, wherein said inner hollow member is attached to a proximal end of said compartment and extends through said compartment into said outer hollow member, and said compartment is adapted to collapse so that said inner hollow member distal end moves past said outer hollow member distal end and into the sterile environment.

13. The device of claim 12, further comprising a partition forming a distal end of said compartment, said inner hollow member extending from said compartment proximal end through an opening in said partition into said outer hollow member.

14. The device of claim 13, wherein said partition is adapted to disengage from a remainder of said compartment to separate said partition and said outer hollow member from said inner hollow member.

15. The device of claim 1, further comprising a partition forming a distal end of said compartment and separating said reservoir and said outer hollow member, wherein said partition is configured to remain within the non-sterile environment when said outer hollow member penetrates said tissue layer.

16. The device of claim 1, wherein said outer hollow member has a length less than a thickness of said boundary layer.

17. The device of claim 1, further comprising a catheter extending from a proximal end of said compartment, wherein said catheter and said inner hollow member are in fluid communication with each other such that said sterile environment is accessed through said catheter and said inner hollow member.

18. The device of claim 1, wherein said outer hollow member distal end includes a seal adapted to be broken by said inner hollow member distal end.

19. A device for performing a sterile medical procedure, comprising:
   an outer hollow member having a sharp distal end for penetrating a tissue separating a sterile environment from a non-sterile environment, the outer hollow member having a seal at the sharp distal end; and
   an inner hollow member within the outer hollow member and axially movable with respect to the outer hollow member, the inner hollow member having a sharp distal end for penetrating the seal and the tissue and extending into the sterile environment.

20. The device of claim 19, wherein the outer hollow member has a length so that the outer hollow member does not extend into the sterile environment.

21. The device of claim 19, further comprising a compartment coupled to the inner hollow member, the compartment defining a reservoir in selective fluid communication with a lumen of the outer hollow member.

22. The device of claim 21, wherein the compartment includes a partition defining a distal end of the reservoir.

23. The device of claim 22, wherein the partition includes at least one hole for permitting fluid communication between the reservoir and the lumen of the outer hollow member.

24. The device of claim 23, further comprising a breakable seal between the at least one hole and the lumen of the outer hollow member.

25. The device of claim 21, wherein the compartment is collapsible.

26. The device of claim 19, further comprising a sealing cap configured to seal said outer hollow member after a medical procedure has been performed.

27. The device of claim 19, further comprising a catheter configured to be in fluid communication with a lumen of the inner hollow member to provide access from the non-sterile environment to the sterile environment.

28. The device of claim 19, wherein said outer hollow member is made of a biodegradable material.

29. The device of claim 19, wherein said inner hollow member is configured to be separated from said outer hollow member after a medical procedure is performed.

30. A method of performing a sterile medical procedure, comprising the steps of:
penetrating a boundary with a distal end of an outer hollow member, said boundary separating a non-sterile environment from a sterile environment;
extending a distal end of an inner hollow member past said outer hollow member distal end and into said sterile environment, said inner hollow member moveably disposed within said outer hollow member; and
establishing fluid communication between a compartment for holding a fluid and said outer hollow member such that the fluid flows through a portion of said outer hollow member surrounding the inner hollow member.

31. The method of claim 30, wherein during said step of fluid communication, the fluid sterilizes said inner hollow member and the boundary surrounding said outer hollow member.

32. The method of claim 30, wherein the establishing step includes collapsing said compartment.

33. The method of claim 30, wherein said outer hollow member does not enter said sterile environment during said penetrating step.

34. The method of claim 30, wherein said inner hollow member distal end breaks a seal on said outer hollow member distal end during said extending step.

35. The method of claim 30, wherein the establishing step includes flowing fluid through a partition that separates a reservoir defined by the compartment from said outer hollow member.

36. The method of claim 35, wherein the establishing step includes flowing fluid through perforations of said partition.

37. The method of claim 35, wherein the establishing step includes breaking a fluid seal between said partition and said outer hollow member.

38. The method of claim 35, wherein said partition remains within the non-sterile environment during the extending and establishing steps.

39. The method of claim 30, further comprising the step of disengaging said outer hollow member from said inner hollow member.

40. The method of claim 39, further comprising the step of sealing a proximal end of said outer hollow member so that said sterile environment is sealed from said non-sterile environment after said disengaging step.

41. The method of claim 30, further comprising the step of providing a catheter extending from a proximal end of said compartment, wherein said catheter and said inner hollow member are in fluid communication with each other.

42. The method of claim 41, further comprising the step of accessing said sterile environment through said catheter and said inner hollow member to perform the medical procedure in said sterile environment.

43. A method of performing a sterile medical procedure, comprising the steps of:

penetrating a tissue separating a sterile environment from a non-sterile environment with a sharpened distal end of an outer hollow member, said distal end including a seal; and
extending a sharpened distal end of an inner hollow member in an axial direction with respect to the outer hollow member such that said sharpened distal end penetrates the seal and the tissue; and
further extending the distal end of the inner hollow member into the sterile environment.

44. The method of claim 43, wherein the outer hollow member distal end does not enter the sterile environment during the penetrating step.

45. The method of claim 43, further comprising the step establishing fluid communication between a reservoir and a lumen of the outer hollow member, the reservoir being defined by a compartment coupled to said inner hollow member.

46. The method of claim 45, wherein a partition defines a distal end of the reservoir and the compartment.

47. The method of claim 46, wherein the partition includes at least one hole for establishing the fluid communication between the reservoir and the lumen of the outer hollow member.

48. The method of claim 47, wherein the step of establishing fluid communication includes breaking a seal provided between the at least one hole and the lumen of the outer hollow member.

49. The method of claim 45, wherein the step of establishing fluid communication includes collapsing the compartment.

50. The method of claim 43, further comprising the step of removing said inner hollow tube and sealing said outer hollow member after performing the medical procedure.

51. The method of claim 43, further comprising the step of accessing said sterile environment through a catheter in fluid communication with a lumen of said inner hollow member.

52. A device for performing sterile medical procedures, comprising:
an outer hollow member including a distal end capable of penetrating a boundary layer separating a non-sterile environment from a sterile environment;
an inner hollow member moveably disposed within the outer hollow member, said inner hollow member including a distal end adapted to extend past said outer hollow member distal end and into a sterile environment; and
a compartment defining a reservoir in selective fluid communication with said outer hollow member, wherein said compartment is adapted to collapse.

53. A method of performing a sterile medical procedure, comprising the steps of:
penetrating a boundary with a distal end of an outer hollow member, said boundary separating a non-sterile environment from a sterile environment;
extending a distal end of an inner hollow member past said outer hollow member distal end and into said sterile environment, said inner hollow member moveably disposed within said outer hollow member; and
establishing fluid communication between a compartment for holding a fluid and said outer hollow member such that the fluid flows through said outer hollow member, wherein the establishing step includes collapsing said compartment.

* * * * *